United States Patent [19]

Aubert

[11] 3,995,025

[45] Nov. 30, 1976

[54] COSMETOLOGICAL PRODUCT CONTAINING EMBRYONIC NECTON

[75] Inventor: Maurice Aubert, Cros de Cagnes, France

[73] Assignee: Societe Anonyme Bonetti, Malakoff, France

[22] Filed: Apr. 18, 1975

[21] Appl. No.: 569,389

[52] U.S. Cl. .................................. 424/95; 424/63; 424/177; 424/359; 424/70
[51] Int. Cl.² ................... A61K 35/12; A61K 7/32; A61K 7/06
[58] Field of Search ........................... 424/95, 63, 70

[56] References Cited

FOREIGN PATENTS OR APPLICATIONS

| 1,272,933 | 8/1961 | France .................................. 424/95 |
| 712,288 | 8/1966 | Italy ...................................... 424/95 |
| 447,268 | 5/1936 | United Kingdom ................... 424/95 |

*Primary Examiner*—Donald B. Moyer
*Attorney, Agent, or Firm*—Young & Thompson

[57] ABSTRACT

A cosmetological cream having trophodynamic properties with respect to skin tissue, comprises 1 to 100 grams of embryonic necton per kilogram of cream.

1 Claim, No Drawings

COSMETOLOGICAL PRODUCT CONTAINING EMBRYONIC NECTON

The present invention concerns a cosmetological product in the nature of a skin cream containing marine biological substances and having a eutrophic action on the organic tissues of living beings.

It is already known to use cosmetological products containing plankton recovered in bulk from the sea and mixed with crushed algae in seawater. However, the present invention relates to preparations having even more specific and efficacious qualities, containing marine biological materials, and in particular utilizing embryonic necton.

The embryonic necton used in the present invention may be gathered from the sea or else cultivated. They are comprised in large part by the larval or embryonic stages of certain marine animals such as teleostei, crustacea, etc. These species may be harvested from the sea or produced in cultivating tanks or basins after fertilization of the eggs. In the latter case, the organisms are developed under culture conditions such as composition of the culture medium, temperature, oxygenation, etc., that are appropriate for the chosen species.

Necton are distinguished from plankton in that the former can swim against the water current while the latter cannot.

The biological materials thus recovered are treated to acquire the active constituents thereof, among them sterols, etc. To this end, there is used the techniques of low temperature freezing, vacuum drying, and pH control. Crushing following by solvent extraction permits recovery of active liposoluble and hydrosoluble substances. Finally, the solution thus obtained may be incorporated in an excipient or cosmetological base permitting absorption by the skin.

The composition produced in this way contains on the one hand substances which activate the cellular metabolism; on the other hand, the composition contains nutritive substances having a trophodynamic action on the cells of the skin, particularly oligo-elements which are found in high concentration in marine creatures because they have lived in the sea. These substances are made available by the preparation technique recited hereinafter. The use of an appropriate cosmetological base promotes the absorption by the skin. There is thus obtained a very effective action for the care of the skin, the mucous membranes and the scalp.

The active ingredients of the composition may comprise for example 90% by weight of embryonic necton comprised by clupeidae larvae, and crustacea larvae 10% by weight. So as to obtain a product having constant characteristics, it is preferable to cultivate the biological elements rather than harvesting them from the sea. Thus the 10% of crustacea may desirably be copepoda which are easy to cultivate and make it possible to obtain a constant product.

The marine organisms, once harvested, are lyophilized and then finely crushed so as to obtain a powder. This powder is extracted in water and alcohol, to separate the hydrosoluble substances and the liposoluble substances, respectively. The two solutions are then filtered to remove membranes and other solids and incorporated in a cream based on lanolin or glycerin.

It is also possible to omit the solvent extraction phase and to crush very finely the embryonic necton to a powder. In this form, the product may be directly incorporated in an excipient cream, a preferred composition of which, for 10 kilograms of product, is as follows:

Stearin 1050 grams
Glycerin 370 grams
Oil of vaseline, i.e. petrolatum 660 grams
Isopropyl myristate 730 grams
Preservative 29 grams (15 grams of methyl p-oxybenzoate and 14 grams of propyl p-oxybenzoate)
Emulsifier 240 grams (120 grams each of cetyl and stearic polyoxyethylenated esters)
Sea salt 6 grams
Water Q.S. to 10 kilograms product.

The powder referred to above, of embryonic necton, is incorporated in this cream in the amount of 1–100 grams per kilogram, depending on the concentration it is desired to provide.

Although the present invention has been described in connection with preferred embodiments, it is to be understood that modifications and variations may be resorted to without departing from the spirit of the invention, as those skilled in this art will readily understand. Such modifications and variations are considered to be within the purview and scope of the present invention as defined by the appended claims.

What is claimed is:

1. A trophodynamic cosmetic skin cream consisting essentially of a base of lanolin or glycerin and 1–100 grams per kilogram of said base of lyophilized and finely crushed embryonic necton consisting essentially of 90% by weight clupeidae larvae and 10% by weight crustacea larvae.